US012678350B2

(12) United States Patent (10) Patent No.: US 12,678,350 B2
Laskin (45) Date of Patent: Jul. 14, 2026

(54) EMERGENCY MEDICAL SUPPLY KIT

(71) Applicant: Bryan Laskin, Wayzata, MN (US)

(72) Inventor: Bryan Laskin, Wayzata, MN (US)

( * ) Notice: Subject to any disclaimer, the term of this patent is extended or adjusted under 35 U.S.C. 154(b) by 17 days.

(21) Appl. No.: 17/969,357

(22) Filed: Oct. 19, 2022

(65) Prior Publication Data

US 2023/0124963 A1 Apr. 20, 2023

Related U.S. Application Data

(60) Provisional application No. 63/257,704, filed on Oct. 20, 2021.

(51) Int. Cl.
A61F 17/00 (2006.01)

(52) U.S. Cl.
CPC .................................... A61F 17/00 (2013.01)

(58) Field of Classification Search
CPC ......... A47B 67/04; A61B 50/13; A61B 50/10; A61F 17/00; B25H 3/028
USPC .......... 206/570, 803, 349–383; 312/209, 206
See application file for complete search history.

(56) References Cited

U.S. PATENT DOCUMENTS

| | | | | |
|---|---|---|---|---|
| 2,999,583 A | * | 9/1961 | Mancini ................... | A61F 17/00 |
| | | | | 206/459.5 |
| 3,128,136 A | * | 4/1964 | Mancini ................... | A61F 17/00 |
| | | | | 312/257.1 |

| | | | | |
|---|---|---|---|---|
| 3,969,006 A | * | 7/1976 | Brown ..................... | A61F 17/00 |
| | | | | 24/67 R |
| 4,640,560 A | * | 2/1987 | Blum ..................... | A61J 7/0481 |
| | | | | 116/72 |
| 6,733,095 B1 | * | 5/2004 | Rieb ........................ | A61J 1/03 |
| | | | | 312/138.1 |
| 7,044,569 B1 | * | 5/2006 | Relyea ................ | B60B 33/0073 |
| | | | | 312/348.3 |
| 9,211,233 B2 | * | 12/2015 | Shavelsky ................. | A61J 7/04 |
| 10,105,287 B2 | * | 10/2018 | Thomas ................ | A61J 7/0418 |
| 10,299,971 B2 | * | 5/2019 | Michaels ............... | G09B 5/125 |
| 11,300,512 B2 | * | 4/2022 | Moriarty, Jr. .......... | A61B 1/043 |
| 11,612,448 B2 | * | 3/2023 | Gustafson .............. | A45C 13/02 |
| | | | | 206/570 |
| 2003/0201697 A1 | * | 10/2003 | Richardson ............ | A47B 81/00 |
| | | | | 312/330.1 |
| 2004/0206659 A1 | * | 10/2004 | Hennig ................... | E06B 9/115 |
| | | | | 206/570 |
| 2007/0007164 A1 | * | 1/2007 | Lord ..................... | A61J 7/0084 |
| | | | | 206/581 |
| 2007/0075508 A1 | * | 4/2007 | Miller ................. | B62D 63/064 |
| | | | | 280/47.26 |
| 2009/0121591 A1 | * | 5/2009 | Giese ..................... | A61B 50/10 |
| | | | | 312/209 |
| 2009/0206674 A1 | * | 8/2009 | Noguchi ................ | A61B 50/10 |
| | | | | 307/104 |
| 2009/0273259 A1 | * | 11/2009 | Whitney ............... | A47B 88/40 |
| | | | | 312/334.44 |

(Continued)

*Primary Examiner* — Chun Hoi Cheung
(74) *Attorney, Agent, or Firm* — Padda Law Group

(57) ABSTRACT

Emergency medical supply kits and methods of using emergency medical supply kits including a housing and a plurality of compartments. Each of the plurality of compartments are independently accessible from outside of the kit, such as on a front of the kit, and include one or more medical supplies. The compartments are labeled on an exposed face, such as a front face, of the compartments to visibly identify the medical supplies from outside the kit.

2 Claims, 5 Drawing Sheets

(56)         References Cited

U.S. PATENT DOCUMENTS

2010/0230304 A1*    9/2010  Plutsky .................. A45C 11/18
                                                      206/307
2012/0080857 A1*    4/2012  Smith ..................... A45C 5/14
                                                      312/209
2012/0185276 A1*    7/2012  Shah .................... A61M 15/009
                                                      206/570
2014/0001078 A1*    1/2014  Andrews ............... A61J 7/0084
                                                      206/534
2014/0311944 A1*   10/2014  Michaels ............... G09B 19/24
                                                      206/570
2016/0030261 A1*    2/2016  Martin ................... A61F 17/00
                                                      206/570
2016/0136049 A1*    5/2016  Weinstein ............. B65D 25/04
                                                      206/570
2019/0125471 A1*    5/2019  Di Benedetto ...... A01N 1/0273
2019/0298475 A1*   10/2019  Holstein ................. A61F 17/00
2020/0337794 A1*   10/2020  Hall ................... A61B 5/02055

* cited by examiner

EMERGENCY MEDICAL SUPPLY KIT

TECHNICAL FIELD

The present invention generally relates to an emergency medical supply kit. In particular, the invention relates to an organized system having a plurality of compartments that contain one or more medical supplies for treating medical emergencies such as emergencies with life threatening severity.

BACKGROUND

In the field of emergency medical care, a number of emergency medical kits have been developed for rendering medical treatments in emergency situations. Various emergency medical procedure kits have been used for packaging, storing and in transporting of medical supplies. Currently available emergency medical kits are generally portable containers with handles, flip top lids and an interior storage space full of medical supplies and medical equipment. However, the various medical supplies and medical equipment are often contained inside the emergency medical kits in an unorganized manner within the storage space of the container. While using the emergency medical procedure kits during a medical emergency, the user opens the kit and searches for a medical supply and medical equipment in the kit as needed in a particular situation. However, the presence of extra medical supplies and equipment not required in the particular medical procedure delay the process of finding the desired supplies and providing a treatment in an emergency medical situation. This searching process is time consuming and particularly difficult during a stressful emergency situation in which time is of the essence. Furthermore, the loss of time due to searching for and dispensing the required medical supplies can potentially be fatal for the person suffering the emergency. In addition, when supplies are used, it may be difficult to realize that items are missing and need to be replaced.

In addition, when all of the medical supplies are stored together in a single container, the unused medical supplies and equipment are subject to contamination during use of the kit. Such contamination can compromise the sterility of the medical supplies and equipment stored inside the emergency medical kits, which may create a risk during future emergencies or require that all of the components of the kit be discarded.

In light of the foregoing disadvantages, improved emergency medical kits are needed to enable both professional as well as non-professional persons to render emergency medical procedures as quickly and easily as possible during emergency situations.

SUMMARY

The objective of the present invention is to provide a much needed and highly organized emergency medical supply kit having a plurality of compartments or components that contain one or more medical supplies for treating medical emergencies of life-threatening severity. The medical supplies are easy to find and quick to access. This organization and arrangement of the medical supplies saves precious time during emergency situations.

In various embodiments, the emergency medical supply kit includes a housing and a plurality of compartments. Each of the plurality of compartments may be independently accessible from outside of the kit and may include one or more medical supplies, and each of the plurality of compartments may be labeled to visibly identify the medical supplies from outside the kit. The plurality of compartments may be slidably removable from the kit. The kit may additionally include wheels provided at the bottom of the housing and/or a handle at the top of the housing. The kit may also include instructions which may be at the top of the housing. The supplies which are highest priority and most urgently needed in likely emergency scenarios may be located in the easiest to find locations, such as in the four front corners of the emergency medical supply kit.

In some embodiments and emergency medical supply kit includes a housing, a plurality of compartments, wherein each of the plurality of compartments are independently accessible from outside of the kit and comprise one or more medical supplies, with each compartment labeled to visibly identify the medical supplies from outside the kit. The one or more of the plurality of compartments may be individually slidably removable from the kit. The kit may also have a plurality of wheels at the bottom of the housing and/or may have a handle at a top of the housing. The kit may also include instructions, which may be provided, for example, on a top of the housing.

In some embodiments, the front of the kit includes four outer corners, and the medical supplies which are highest priority are provided in the four front corners of the emergency medical supply kit. The medical supplies included in the kits may selected and provided on the basis of a location of use of the medical supply kit. The position of the compartments including the medical supplies may be selected and provided on the basis of a location of use of the medical supply kit.

In various other embodiments, the emergency medical supply kit includes a housing, a plurality of wheels provided at the bottom of the housing, a handle provided at a top of the housing, and instructions provided at a top of the housing. The plurality of compartments may each be independently accessible from a front of the kit and may include or more medical supplies. Each of the compartments may be labeled to visibly identify the one or more medical supplies from outside the kit. In some such embodiments, the compartments may be individually slidably removable from the kit.

In still other embodiments, the emergency medical supply kit may include a housing and a plurality of compartments contained within the housing. Each of the compartments may be independently accessible from outside of the kit and may include one or more medical supplies. Each compartment may be labeled to visibly identify the medical supplies from outside the kit. The kit may further include a communications module configured for wireless communication with the internet and a power source. Such kits may also include a user interface configured to contact emergency services at the direction of a user. The user interface may include a button, wherein emergency services are contacted when a user presses the button. The kits may further include a GPS location component such that contacting emergency services automatically includes providing a location of the emergency medical supply kit.

In some embodiments, the emergency medical supply kit may include one or more sensors configured to detect use of the emergency medical supply kit by a user. For example, the kit may be configured to automatically contact emergency services when the one or more sensors detects use of the medical supply kit, such as when the one or more sensors detect removal of one of the medical supplies from the medical supply kit. The emergency medical supply kit may automatically transmit data relating to the removal of the one or more medical supplies to a separate system. Transmission of the data may automatically result in a replacement medical supply being ordered for the medical supply kit.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

Figure 1:
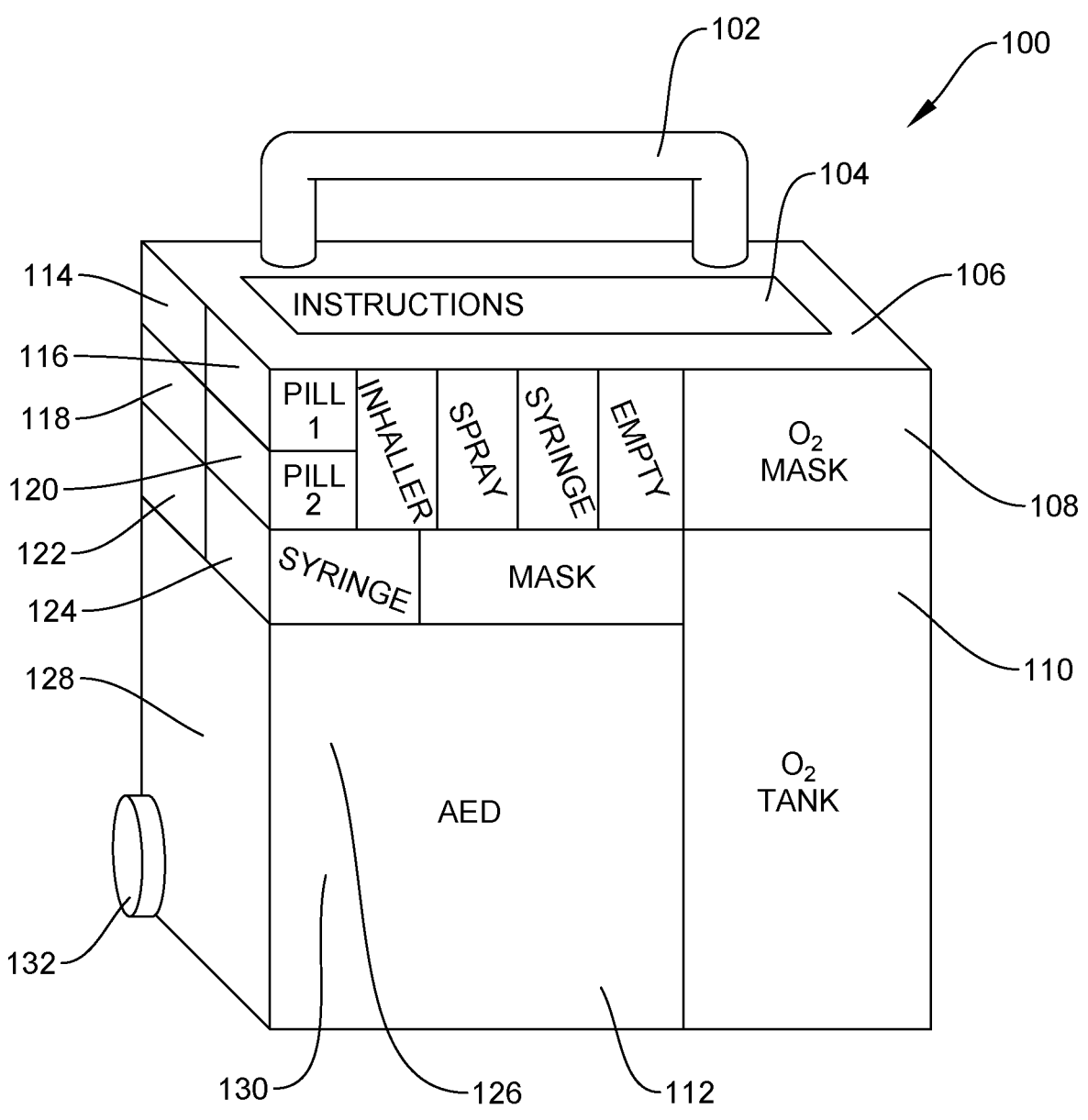
FIG. 1 is a perspective view of an emergency medical supply kit in accordance with some embodiments of the present disclosure.

To facilitate understanding, identical reference numerals have been used, where possible, to designate identical elements that are common to the figures. The figures are not drawn to scale and may be simplified for clarity. Elements and features of one embodiment may be beneficially incorporated in other embodiments without further recitation.

DETAILED DESCRIPTION

The embodiments herein and the various features and advantageous details thereof are explained more fully with reference to the non-limiting embodiments that are illustrated in the accompanying drawings and detailed in the following description. The description used herein are intended to facilitate an understanding of ways in which the embodiments herein may be practiced and to further enable those of skill in the art to practice the embodiments herein. Accordingly, the description or explanation should not be construed as limiting the scope of the embodiments herein. Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown but is to be accorded the widest scope consistent with the claims.

Exemplary embodiments are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. While embodiments of the present invention have been illustrated and described, it will be clear that the invention is not limited to these embodiments only. Numerous modifications, changes, variations, substitutions, and equivalents will be apparent to those skilled in the art, without departing from the spirit and scope of the invention, as described in the claim.

The present disclosure relates generally to an organized emergency medical supply kit and the method of accessing the emergency medical kit.

FIG. 1 illustrates a prospective view of an emergency medical supply kit 100 in accordance with various embodiments of the present disclosure. FIG. 1 illustrates a housing 106 with multiple compartments 108, 110, 112, . . . , 130. A plurality of wheels 132 are provided at the bottom of the housing for easy movement and a handle 102 is provided at the top of the housing 106 to carry and move the kit 100.

In an embodiment of the present disclosure, the housing 106 is made up of a material such as plastic, metal, cardboard and/or wood. The housing 106 may be shaped as rectangular, square, or other shapes. The housing 106 may be closed with no compartments on the top, bottom, left, right, and/or back sides. Alternatively or additionally, one or more of the top, bottom, left, right and/or back sides may be formed, in part or entirely, by the compartments 108, 110, 112, . . . , 130 and or have spaces which contain compartments 108, 110, 112, . . . , 130. In such embodiments, the housing 106 may be a frame which holds the compartments 108, 110, 112, . . . , 130 and/or the compartments 108, 110, 112, . . . , 130 may be configured to connect together as discussed further below. In some embodiments, some or all of the housing 106 may be a frame structure and may have various openings, slots or other support structures on the top, bottom, left, right, front and/or back side to hold and/or house the compartments 108, 110, 112, . . . , 130. In still other embodiments, some or all of the compartments 108, 110, 112, . . . , 130 may be formed integrally with the housing, such as from the same material as the housing. Such compartments 108, 110, 112, . . . , 130 may include covers, lids, or doors, for example, to access the medical supplies within the compartments 108, 110, 112, . . . , 130.

The front side of the kit 100 may include all of the compartments 108, 110, 112, . . . , 130, which may all be accessed from the front side of the kit to obtain the medical supplies during an emergency. However, the kit 100 may alternatively include one or more compartments 108, 110, 112, . . . , 130 on the sides, top, back, and/or bottom of the kit 100, and the supplies provided by such compartments 108, 110, 112, . . . , 130 may be accessed accordingly through the side, top, back or bottom of the kit 100. The medical supplies contained in such compartments 108, 110, 112, . . . , 130 located on sides of the kit 100 that are not the front may be lower priority supplies for which more time is available to locate them without creating a risk for the patient.

The compartments 108, 110, 112, . . . , 130 may be containers which hold the medical supplies and may or may not be integral with the housing 106. For example, the compartments 108, 110, 112, . . . , 130 may be rectangular containers having a top, bottom, and four sides. One of the four sides may form the front, exposed face of the compartment 108, 110, 112, . . . , 130, for compartments 108, 110, 112, . . . , 130 located on the front of the kit. For compartments on the top of the kit, the top of the container may be the exposed face. The front or top of the container may be a lid which may be removable or may flip to open the compartment 108, 110, 112, . . . , 130, for example. Alternatively, the compartments 108, 110, 112, . . . , 130 may themselves be separate components which are entirely removable from the emergency medical supply kit 106 and may be the medical supplies or may contain the medical supplies. For example, compartment 116 which is labelled "PILL 1" may be a compartment such as a sliding drawer which may contain pill 1, which may be loose pills within compartment 116 or may be contained in a bottle, packet or other container inside compartment 116. Alternatively, compartment 116 may be a removable element which itself acts as a container for pill 1. That is, compartment 116 may be a pill container which may include a safety cap in the manner of traditional pill bottles. The compartments 108, 110, 112, . . . , 130 which themselves are removable medical supply containers may include attachment pieces at or along their sides to engage with the housing 106 framework and/or with adjacent compartments 108, 110, 112, . . . , 130. Once the compartment 108, 110, 112, . . . , 130 which is itself a medical supply component or a container for a medical supply component, is removed from the housing 106, the medical supply may be ready for use with no additional time spent opening containers.

One or more of the compartments 108, 110, 112, . . . , 130 may slidably connect with the housing 106 or with adjacent compartments 108, 110, 112, . . . , 130. For example, the compartment 108, 110, 112, . . . , 130 may simply fit within a cavity in the housing 106, and/or the cavity which holds the compartment 108, 110, 112, . . . , 130 may be formed by the space between the adjacent compartments 108, 110, 112, . . . , 130, and the cavity may be sized to closely and slidably accommodate the compartment 108, 110, 112, . . . , 130. Alternatively, the compartment 108, 110, 112, . . . , 130 may include a feature on each lateral side of the compartment 108, 110, 112, . . . , 130 which slidably engages with a feature of the housing 106 or adjacent compartments 108, 110, 112, . . . , 130 within the space, such as sliders, lips, rails, ledges, or grooves. In some embodiments, compartments 108, 110, 112, . . . , 130 and/or the housing 106 may include features which allow the compartments 108, 110, 112, . . . , 130 to click or snap to the housing 106 or to each other to hold them in place.

In some embodiments, the kit may further include safety features to prevent easy access to the supplies stored within the kit, such as child safety features. Such features may be a part of the sliding or clicking or snapping or other mating mechanism of one or more of the compartments 108, 110, 112, . . . , 130, or may be a separate element such as a child safe cap, to keep one or more of the supplies secure until needed by a competent adult.

In various embodiment of the present disclosure, the housing 106 occupies a minimal volume and footprint for ease of storage in all types of places where medical emergencies may occur, such as locations where large numbers of people are together away from home. Furthermore, the emergency medical supply kit 100 may be stored and used in various types of environments, to be available for use quickly on an as needed basis. For example, the emergency medical supply kit 100 may be stored and used at medical facilities including but not limited to dentist's offices, physician's offices, nursing homes, and rehabilitation centers. They may also be stored and used at non-medical facilities such as health clubs, camps, offices, stores, airports, restaurants, schools, homes, public transit stations and on board public transit like buses, planes, ambulances, trucks and automobiles.

The emergency medical supply kit 100 may be customized and configured based on a location at which the emergency medical supply kit 100 is to be used and the type of people and emergency situations which are most likely to occur at that location. For example, the supplies included in the medical supply kit 100, and the configuration of those supplies, may be selected and provided based upon the location at which the medical supply kit 100 is designed to be used. For example, a medical supply kit 100 configured for use in restaurants may provide particular medical supplies, or additional supplies and/or a different prioritizes location of supplies used for medical emergencies more likely to occur in restaurants, such as emergencies related to food allergies, choking, and cut and burn injuries. An emergency medical supply kit 100 for use at an outdoor location such as a camp may include and/or be configured to prioritize access to supplies for anaphylactic reactions such as epinephrine pens and antihistamines such as Benadryl. An emergency medical supply kit 100 for use at locations where there is a risk for cardiac events, such as at medical service providers, retirement communities and nursing homes may include additional supplies and/or may prioritize access to supplies for cardiac resuscitation such as defibrillators, oxygen and oxygen masks. The medical supply kit 100 which is customized as per location may include particular medical supplies and/or prioritize the configuration of supplies as needed for emergency events which are most likely occur at such locations, while optionally still providing general emergency supplies and equipment which may be needed at any location such as syringes, antiseptics, defibrillators, and/or oxygen.

The locations of supplies of highest priority may be on the front of the kit 100. By displaying all high priority compartments 108, 110, 112, . . . , 130 on the front of the kit, a user can quickly and easily perform a visual scan through the items to find what they need. In addition, the highest priority supplies, such as those most likely to be needed, or those most likely to be needed very quickly, may be located in the easiest to see locations, such as closest to the top of the kit 100 or at the top front corners or one of the four front corners of the kit 100. Furthermore, emergency medical supply kits 100 which are configured for a particular location may be uniformly provided in the same standard configuration for that location. In this way, a user who is familiar with the kit 100 can reliably find the desired medical supply, at the same location within the kit 100 every time, to save precious time in an emergency.

In some embodiments, the medical supply kit 100 is a single use kit and is disposable after use, regardless of how much or how little of the supplies are used. In other embodiments, the medical supply kit 100 is reusable and the medical supplies may be refilled or replaced after use. For example, if one or more compartments 108, 110, 112, . . . , 130 are used during an emergency event, those used compartments 108, 110, 112, . . . , 130 and/or their contents may be individually replaced with new compartments 108, 110, 112, . . . , 130 and/or their contents. In addition, the use of multiple separate and self-contained compartments 108, 110, 112, . . . , 130 may prevent the contamination of other compartments 108, 110, 112, . . . , 130, including adjacent compartments 108, 110, 112, . . . , 130, when one compartment 108, 110, 112, . . . , 130 is used during an emergency.

In various embodiments, the emergency medical supply kit 100 includes compartments 108, 110, 112, . . . , 130 and each compartment 108, 110, 112, . . . , 130 is independently accessible from the outside of the outside of the medical supply kit 100 and contains one or more medical supplies. For example, in the embodiments shown in the figures, all of compartments 108, 110, 112, . . . , 130 are accessible only on the front of the emergency medical supply kit 100. However, in alternative embodiments, some compartments, such as those providing components which are less likely to be needed or for which there may be less need to obtain them quickly, may be accessible only through the top, back, left or right side of the emergency medical supply kit 100.

In various embodiments such as the embodiment shown in FIG. 1, the compartments 108, 110, 112, . . . , 130 may be marked or labeled to indicate a type of medical supply or supplies contained in each of the compartments 108, 110, 112, . . . , 130. In various embodiments, the indication of the type of medical supply contained in each compartment 108, 110, 112, . . . , 130 may be provided by means of a printed label or sticker provided on the exposed face of the compartment 108, 110, 112, . . . , 130, such as on the front of each compartment 108, 110, 112, . . . , 130 and/or by directly marking on the exterior outside face of the compartment 108, 110, 112, . . . , 130 itself. In various embodiments, the indication of the type of medical supply contained in the compartment 108, 110, 112, . . . , 130, is provided by methods such as, but not limited to, printing on the surface of the top cover of the compartments 108, 110, 112, . . . , 130, etching, laser cutting, and so on. The indication may be words, abbreviations, symbols, and/or images, for example.

In various embodiment, the compartments 108, 110, 112, . . . , 130 and the housing 106 are made of a material that is relatively rigid. In various embodiment, one or more or all of the compartments 108, 110, 112, . . . , 130 may be made of a material that is either transparent or opaque. For example, the outside face of the compartments 108, 110, 112, . . . , 130 or the entire compartments 108, 110, 112, . . . , 130 may be transparent or opaque. The compartments 108, 110, 112, . . . , 130 may be removable compartments 108, 110, 112, . . . , 130 and/or may be connected to the housing 106. Each compartment 108, 110, 112, . . . , 130 may be provided in an individually closed and/or enclosed state, such as a waterproof and airtight state, in order to prevent contamination of the medical supplies contained therein. This closure or enclosure may also prevent contamination of unused compartments 108, 110, 112, . . . , 130 when other compartments 108, 110, 112, . . . , 130 are used.

The compartments 108, 110, 112, . . . , 130 containing one or more medical supplies are organized for a particular type of medical emergencies or treatment situations including but not limited to bleeding (hemorrhage, hypovolemia, internal bleeding), breathing difficulties (asthma attacks, allergic reactions), bites, burns, stings, epileptic seizure, cardiac arrest, myocardial infraction (heart attack), cerebrovascular accidents (strokes), etc.

In some embodiments, the medical supplies contained in the compartments 108, 110, 112, . . . , 130 may include but are not limited to bandages such adhesive bandages, cotton balls, topical medicines, orthopedic products such as compression wraps, oral medicines, injectable medicines, syringes, antiseptics such as alcohol wipes, compact oxygen tanks, automated electronic defibrillator (AED) devices, oxygen masks, masks, inhalers, various solutions, etc.

In various embodiment, the compartments 108, 110, 112, . . . , 130 are configured to allow for easy access to, and replacement of, one or more of the compartments 108, 110, 112, . . . , 130 individually and/or the medical supplies contained in the compartments 108, 110, 112, . . . , 130 of the kit 100.

In various embodiments, the positions of the compartments 108, 110, 112, . . . , 130 in the housing 106 are pre-defined and fixed. For example, an inhaler may have highest priority in case of an asthma attack, hence the inhaler may be located in easily accessible locations such as in the topmost row or in one of the four corners of the emergency medical supply kit.

In various embodiments, the type of medical supply and their position in the housing 106 are selected and provided in the kit 100 on the basis of the location of intended use or a type of medical emergency. For example, in camps or restaurants there is an elevated risk of severe allergic reactions due to bees and food allergens and should contain an epinephrine pen in the most accessible regions of the kit 100.

In various embodiment, some or all of the plurality of compartments 108, 110, 112, . . . , 130 may have a closure means, such as, but not limited to, a clickable or snap-in-place lid, flap, etc.

In various embodiments, some or all of the plurality of compartments 108, 110, 112, . . . , 130 are accessible by separately and individually sliding each of the compartments 108, 110, 112, . . . , 130 independently like a drawer from the housing 106 or from their connections to adjacent compartments 108, 110, 112, . . . , 130.

In various embodiments, the kit 100 may include instructions for use of the medical supplies provided in the kit 100. In some embodiments, the instructions may be provided on the housing 106 in an instruction display area 104 for providing user instructions corresponding to one or more first-aid medical procedures in an easy to see location such as the top of the kit 100. In various embodiments, the instructions display area 104 may contain a set of visual written instructions and/or figures for the use of one or more medical supplies contained in the plurality of the compartments 108, 110, 112, . . . , 130 in a printed material such as, but not limited to, a written brochure, label or sticker provided on a top portion of the housing near the handle 102. The language in which the visual written instructions are written may depend on the country in which the emergency medical supply kit is to be used or installed. In some embodiments, the visual written instructions are provided in more than one language which may be commonly used.

In various embodiments, the instructions display area 104 contains a set of visual instructions demonstrating the use of one or more medical supplies contained in the plurality of the compartments 108, 110, 112, . . . , 130 and outlining steps to be performed while providing an emergency treatment in chronological order. In some embodiments, the set of instructions in the instructions display area 104 may include numerals and/or letters to assist with locating the appropriate supplies, and the compartments 108, 110, 112, . . . , 130 may be labeled with the corresponding numbers and/or letters as well as an identification of their components, in alphabetical and/or numerical order to assist with quickly locating the appropriate supply.

In various embodiments, the compartments 108, 110, 112, . . . , 130 and/or their indicators in the kit 100 may be color coded in groups to indicate types of supplies or compartments 108, 110, 112, . . . , 130 to be used in case of a particular medical emergency to assist with quickly finding the appropriate supplies. The instruction provided in the instructions display area 104 may likewise be provided in the same color for the corresponding types of emergencies.

In various embodiments, such as embodiments in which the kit 100 is reusable, instruction 104 may be displayed on a digital display screen or displayed in the form of pre-recorded digital or audio/video instructions corresponding to one of the plurality of emergency scenario elements selected by the user. In various alternative embodiments, the instructions display area 104 may be a touch enabled screen and an emergency scenario may be selected with the help of button icons on the touchscreen.

In various embodiments, the emergency medical supply kit 100 may be operable by both professional and non-professional people to administer medical aid to a patient in an emergency.

Figure 2:
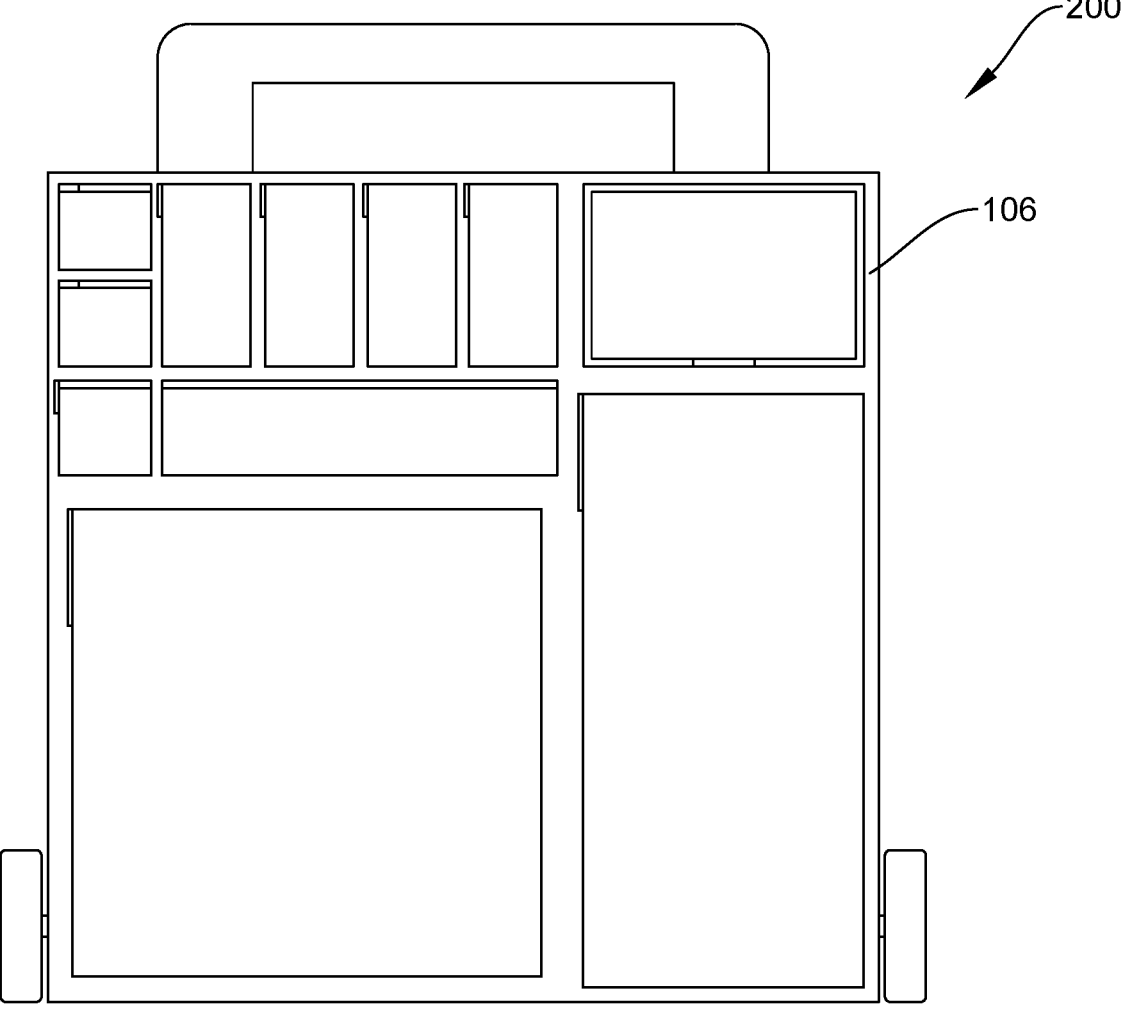
FIG. 2 is a front view of an emergency medical supply kit in accordance with some embodiments of the present disclosure.

FIG. 2 illustrates a front view of an emergency medical supply kit 200 in accordance with various embodiments. The emergency medical supply kit 200 is like that of FIG. 1, except without the compartments 108, 110, 112, . . . , 130 specifically labeled and with a solid housing on the sides. Different particular medical supplies may be provided in the various compartments 108, 110, 112, . . . , 130, which may be labeled and identified accordingly. In addition, the sizes and shapes and configurations of the compartments 108, 110, 112, . . . , 130 are not limited to those shown. Rather, the sizes of the compartments 108, 110, 112, . . . , 130 may vary depending on the customization of the kit 200 as per location of use or as per the type of medical emergency.

Figure 3:
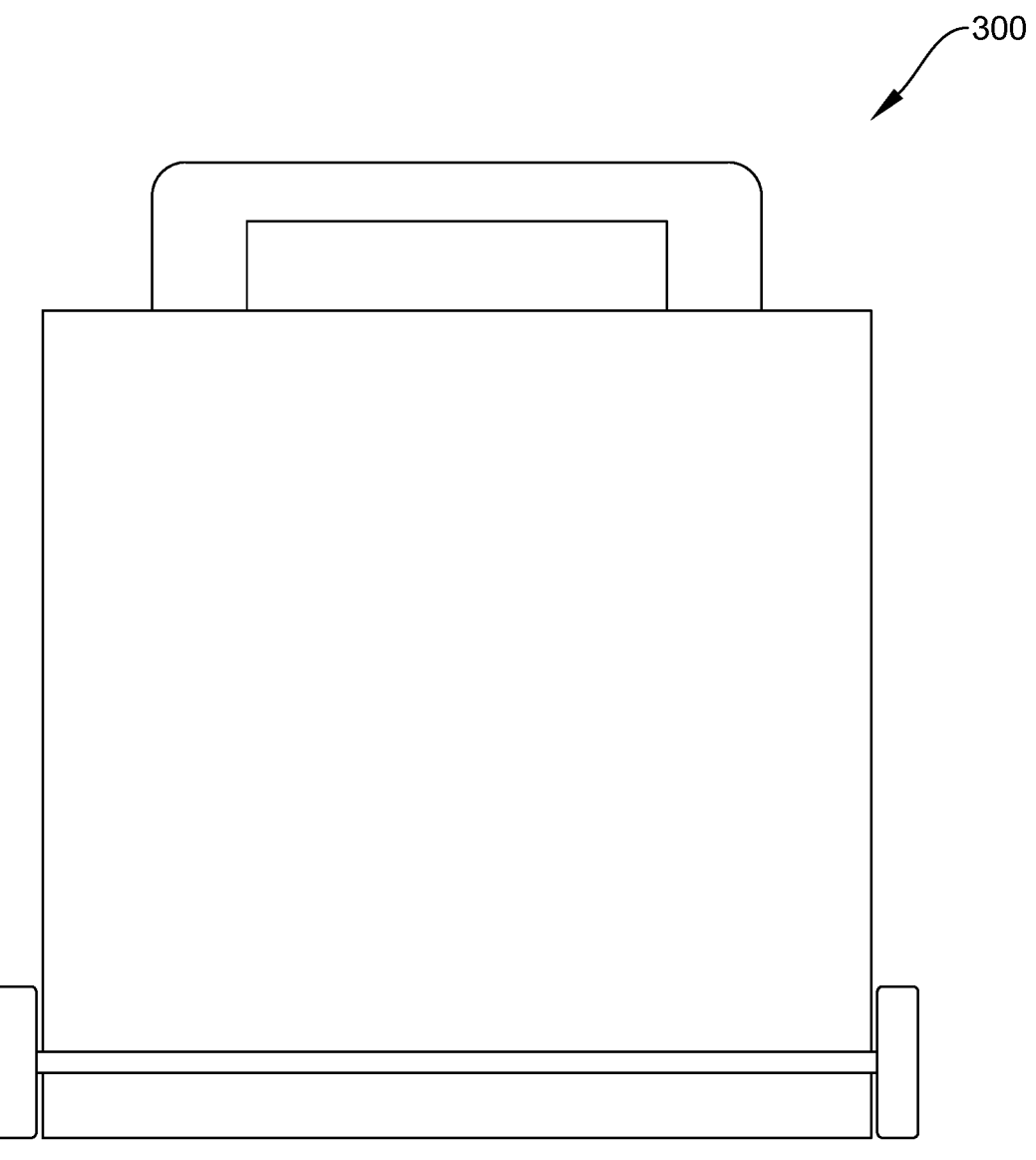
FIG. 3 is a posterior view of the emergency medical supply kit of FIGS. 1 and 2.
Figure 4:
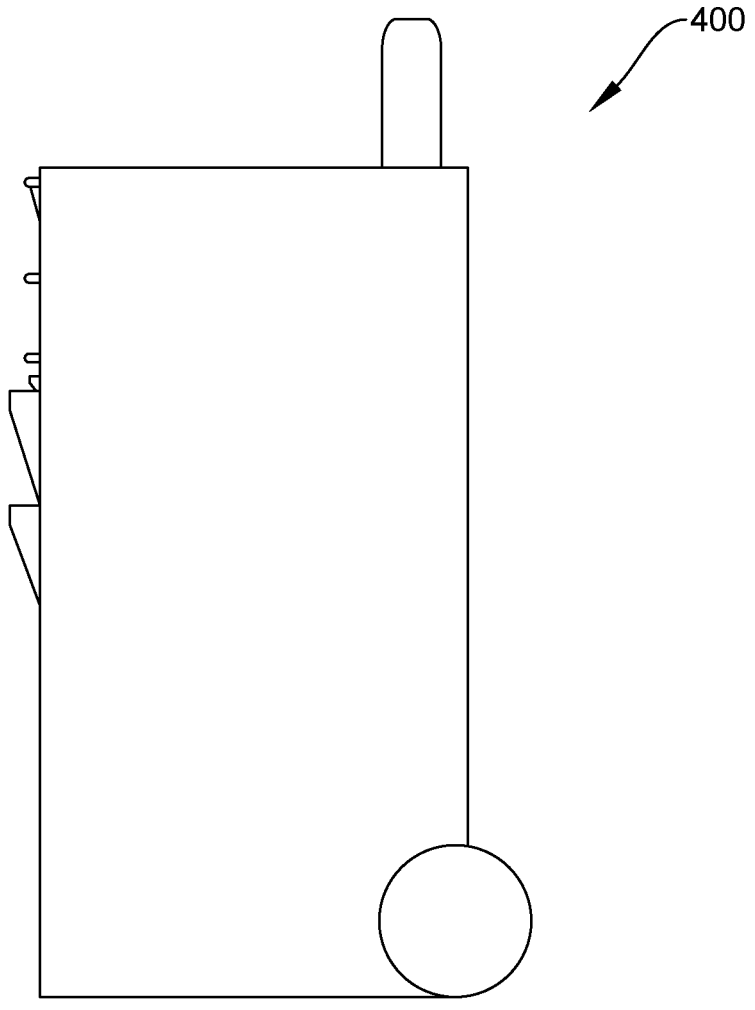
FIG. 4 is a left side view of the emergency medical supply kit of FIG. 2.
Figure 5:
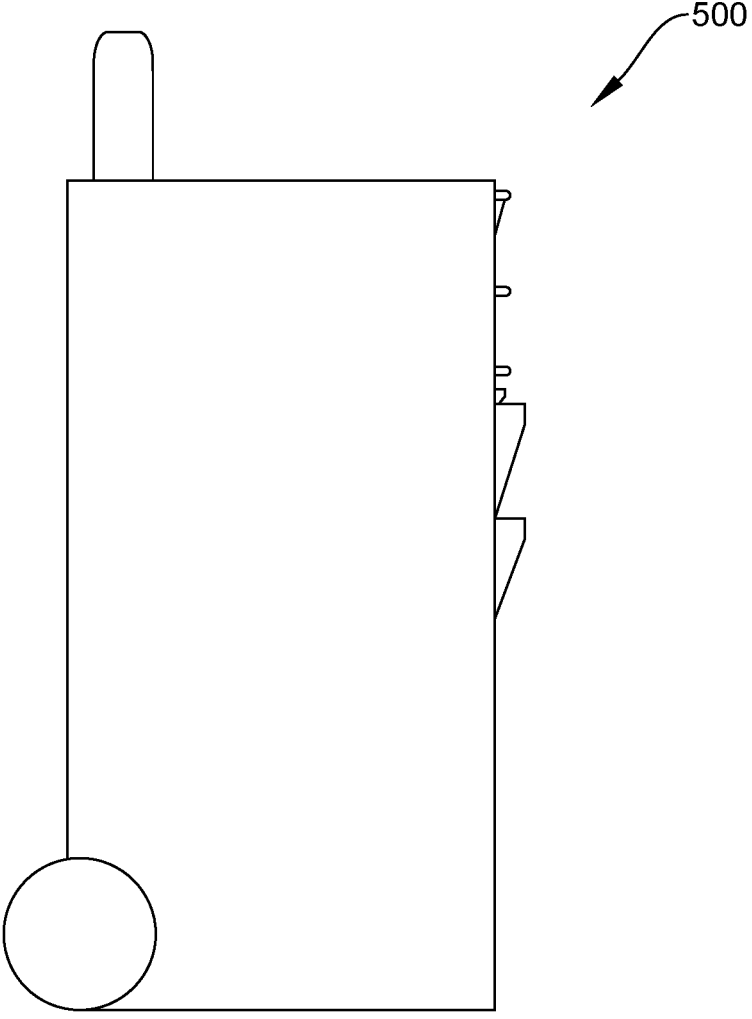
FIG. 5 is a right-side view of the emergency medical supply kit of FIG. 2.

FIGS. 3-5 illustrate alternative views of the medical supply kit 200. FIG. 3 illustrates the posterior view of the emergency medical supply kit 200 in accordance with various embodiments of the present invention. Particularly, FIG. 3 illustrates the posterior side of the emergency medical supply kit 200 that may be a continuous portion of the housing 106 without compartments.

FIG. 4 illustrates the left side view of the emergency medical supply kit 100, 200 in accordance with various embodiments of the present disclosure.

FIG. 5 illustrates the right-side view of the emergency medical supply kit 200 in accordance with some embodiments of the present disclosure.

The posterior and side views of medical supply kit 100 may be like those of medical supply kit 200 shown in FIGS. 3-5, but with the separate compartments visible in the side view and with the posterior view showing additional compartments accessible from the posterior side.

In various alternative embodiments, the medical supply kit, like any of the alternatives described herein as well as other designs, may include electrical components for various purposes as described further below. For example, the medical supply kit may include a user interface such as a touch screen which may be used for controlling a function of the medical supply kit, for communicating with others remotely, for displaying instructions for a user such as instructions related how to use one or more of the medical supplies in the kit, and/or for notifying a user of something, such as that emergency responders have been notified or that they will be notified unless the user takes a particular action. The medical supply kit may further include one or more memory storage devices for data storage and software, for example, and one or more processors for performing various functions including executing the software. In some embodiments, the medical supply kit may include a wireless connection to the internet. For example, the kit may include one or more components for wireless communication such as a communications chip or module, a microprocessor, and a memory chip. The medical supply kit may further include a power supply such as a battery and/or a plug for connection to power outlet which may be used to power the communication system and/or to charge a rechargeable battery which may be the primary power source or may be a backup battery. The communications module may communicate wirelessly such through Wi-Fi, radiofrequency, Blue Tooth, cellular data, or other wireless communication methods. This wireless connection may be used to communicate information about the medical supply kit, such as when it has been used and which compartments 108, 110, 112, . . . , 130 have been used.

In some embodiments, the medical supply kit may include one or more sensors. Examples of sensors which may be included in the medical supply kit include pressure sensors, accelerometers, gyroscope sensors, optical sensors, and proximity sensors. In some embodiments, it may include RFID chips and RFID chip detectors. For example, the medical supplies and/or the compartments 108, 110, 112, . . . , 130 which contain them may include RFID chips unique to the particular medical supplies, while the housing may include one or more RFID chip detectors. The sensors may communicate with the processor for sensing information related to the medical supply kit. For example, one or more of the compartments 108, 110, 112, . . . , 130 may include a sensor which detects when the compartment 108, 110, 112, . . . , 130 is opened by a user. Additionally, or alternatively, one or more medical supplies and/or compartments 108, 110, 112, . . . , 130 containing medical supplies may include a sensor for the medical supply kit to detect when a medical supply is removed from a compartment 108, 110, 112, . . . , 130. In such embodiments, the medical supply kit may use its communication system to transmit sensed information to an outside system, such as a monitoring system which may initiate subsequent steps such as emergency response notifications and/or medical supply orders, for example, either automatically or on demand, such as after user confirmation. The information detected by the sensors may be used for various purposes such detecting that the medical supply kit is in use, for triggering a call to emergency services, for preparing a list of supplies in need of replenishment in the medical supply kit, and/or for ordering replacement medical supplies.

Various embodiments of the medical supply kit may include sensors to detect removal of a medical supply. For example, the medical supplies may include RFID tags, such as on the medical supplies themselves or on their packaging or containers, and the medical supply kit may include a detector. The medical supply kit and/or a remote system in communication with the medical supply kit, may be programmed with information indicating the specific medical supplies in the medical supply kit when fully stocked. When the medical supply kit detects that a medical supply has been removed and/or is missing from the medical supply kit, the medical supply kit, or a monitoring system in remote communication with the medical supply kit, may automatically place an order to replace the missing medical supply which may be delivered to the location of the medical supply kit. Alternatively, the missing medical supply may be placed on a list of items to by ordered at the discretion of a user and/or a message may be sent to a user directing them to order the missing medical supply or requesting confirmation of an order for the replacement medical supply. In some embodiments, the replacement medical supply may not be ordered (or other alternative order related options may not occur) until a certain amount of time passes, such as between 30 minutes and 24 hours or 48 hours, for example. If the medical supply kit detects that a medical supply has been removed and/or is missing from the medical supply kit, but the medical supply is replaced before expiration of the time limit, it may not proceed with any order related steps.

In some embodiments, the wirelessly connected medical supply kit may be configured to automatically notify authorities that it has been opened, such as if one or more compartments 108, 110, 112, . . . , 130 is opened, which may provide an indication of the emergency situation. Such embodiments may further include components for GPS location. The communications module may communicate wirelessly with a router, which may then connect to the cloud and then to an emergency services provider such as a 911 operator or a call center which may then contact a 911 operator. Alternatively, the communications module may communicate with the cloud or directly with an emergency services provider through a cellular communication network. In some such embodiments, the medical supply kit may include one or more sensors which detect when one or more compartments 108, 110, 112, . . . , 130 have been opened. In some embodiments, the medical supply kit may be configured such that opening of any compartment 108, 110, 112, . . . , 130, or only opening of the compartments 108, 110, 112, . . . , 130 which correlate to life threatening emergencies, will be used automatically notify authorities of a possible emergency, such as the opening of a defibrillator compartment. The medical supply kit may be configured such that opening of compartments 108, 110, 112, . . . , 130 which do not correlate with a likely high-risk emergency, such as a compartment containing an antibiotic ointment or an over-the-counter medication, may not result in an automatic notification being sent to authorities.

In some embodiments which are configured to automatically notify authorities of an emergency, the medical supply kit and/or the system to which it is wirelessly connected may be configured to wait a period of time before contacting authorities. For example, there may be a delay of between 1 second and 1 minute, such as about 5-15 seconds, or about 5-10 seconds. During this delay, a user may be able to cancel the notification such that it is not sent. In some such embodiments, the medical supply kit may alert the user of the medical supply kit that authorities are about to be notified and may give the user an opportunity to cancel the notification. For example, the medical supply kit may emit an audible signal such as an alarm or a count down and/or may produce a visual signal such as a flashing light or button, and the user may cancel the notification by pressing the button or through the user interface. In some embodiments the user interface such as a display screen like a touch screen may visually notify the user of the impending notification and may allow a user to input a cancelation order. In still other embodiments, the medical supply kit may allow a user to contact a monitoring system or an emergency service provider to ask for assistance through a user interface, such as by pushing an emergency notification button and/or by interacting with the display screen.

The notification which is wirelessly transmitted to authorities by the medical supply kit may include the location of the medical supply kit, which may be provided through the GPS system within the medical supply kit, as well as the compartments 108, 110, 112, . . . , 130 which have been opened indicating the types of medical supplies which were required. This information may be useful to the emergency responders for determining the type of emergency which is likely occurring.

While multiple embodiments are disclosed, still other embodiments of the present disclosure will become apparent to those skilled in the art from the following detailed description, which shows and describes illustrative embodiments of the disclosure. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

In the foregoing description various embodiments of the invention have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. An emergency medical supply kit, comprising:
   a housing;
   a plurality of wheels provided at the bottom of the housing;
   a handle provided at a top of the housing;
   instructions provided at a top of the housing; and
   a plurality of containers, wherein each of the plurality of containers comprises a plurality of sides and a lid, and wherein each of the plurality of containers are independently accessible and slidably removable from a front of the housing and contain one or more of an individual type of medical supply, the individual medical supplies comprising an epinephrine pen, an antiseptic, and a bandage, and wherein each container is labeled to visibly identify the medical supply from outside the kit, whereby the emergency medical supply kit includes an arrangement to facilitate rendering emergency medical procedures during emergency situations.

2. The emergency medical kit of claim 1 wherein one or more of the plurality of containers is connected to and individually slidably removable from the housing.

* * * * *